United States Patent
Dubois et al.

(10) Patent No.: US 9,790,168 B2
(45) Date of Patent: Oct. 17, 2017

(54) METHOD OF SYNTHESISING AMINO ACID BY METATHESIS, HYDROLYSIS, THEN HYDROGENATION

(71) Applicant: ARKEMA FRANCE, Colombes (FR)

(72) Inventors: Jean-Luc Dubois, Millery (FR); Jean-Luc Couturier, Lyons (FR)

(73) Assignee: ARKEMA FRANCE, Colombes (FR)

( * ) Notice: Subject to any disclaimer, the term of this patent is extended or adjusted under 35 U.S.C. 154(b) by 0 days.

(21) Appl. No.: 14/766,956

(22) PCT Filed: Feb. 10, 2014

(86) PCT No.: PCT/FR2014/050249
§ 371 (c)(1),
(2) Date: Aug. 10, 2015

(87) PCT Pub. No.: WO2014/122412
PCT Pub. Date: Aug. 14, 2014

(65) Prior Publication Data
US 2016/0002147 A1    Jan. 7, 2016

(30) Foreign Application Priority Data
Feb. 8, 2013 (FR) ..................................... 13 51104

(51) Int. Cl.
*C07C 227/04*  (2006.01)
*C07C 253/16*  (2006.01)
*C07C 253/30*  (2006.01)
*C08G 69/10*   (2006.01)

(52) U.S. Cl.
CPC .......... *C07C 227/04* (2013.01); *C07C 253/16* (2013.01); *C07C 253/30* (2013.01); *C08G 69/10* (2013.01)

(58) Field of Classification Search
CPC ... C07C 227/04; C07C 227/18; C07C 253/16; C07C 253/30
See application file for complete search history.

(56) References Cited

U.S. PATENT DOCUMENTS

2010/0168453 A1*  7/2010  Dubois ................. C07C 227/04
                                            554/114
2011/0224454 A1   9/2011  Dubois

FOREIGN PATENT DOCUMENTS

| FR | 1 087 798 A | 2/1955 |
| FR | 1 574 471 | 7/1969 |
| GB | 1 177 154 A | 1/1970 |
| JP | 51-127022 A | 11/1976 |
| WO | WO 2010/055273 A1 | 5/2010 |

OTHER PUBLICATIONS

International Search Report (PCT/ISA/210) dated Apr. 24, 2014, by the European Patent Office as the International Searching Authority for International Application No. PCT/FR2014/050249.
Written Opinion (PCT/ISA/237) dated Apr. 24, 2014, by the European Patent Office as the International Searching Authority for International Application No. PCT/FR2014/050247.

* cited by examiner

*Primary Examiner* — Rachel Kahn
(74) *Attorney, Agent, or Firm* — Buchanan Ingersoll & Rooney P.C.

(57) ABSTRACT

A method of synthesising an amino acid from an unsaturated fatty compound I that includes at least the following steps: cross-metathesis with a short unsaturated compound II, one of compounds I or II comprising a nitrile function and the other of these compounds II or I an ester function, so as to obtain and recover at least one monounsaturated nitrile ester NEU; hydrolysis of the NEU in unsaturated acid nitrile NAU; hydrogenation of the NAU to saturated amino acid AA; and then purification of the AA, if applicable, in particular by crystallisation. Also, a polymer obtained by polymerisation using the amino acid synthesised according to the method.

17 Claims, No Drawings

METHOD OF SYNTHESISING AMINO ACID BY METATHESIS, HYDROLYSIS, THEN HYDROGENATION

FIELD OF THE INVENTION

The invention relates to a process for synthesizing amino acid in high purity from unsaturated fatty esters or nitriles, involving a metathesis step.

TECHNICAL BACKGROUND

Several routes have already been tested for synthesizing amino acid from unsaturated fatty acids, esters or nitriles involving a metathesis step. However, none of the tested sequences of reactions is truly satisfactory.

According to a first tested route, cross metathesis followed by hydrogenation produces an amino ester containing many impurities. Further, if it comprises more than 9 carbon atoms, the amino ester proves to be very difficult to purify, especially with a distillation yield that is largely insufficient to be able to envisage an industrial application.

According to a second tested route, cross metathesis followed by hydrogenation and then hydrolysis of the amino ester obtained for the purpose of producing an amino acid proves to be unachievable in practice, because it is so difficult to hydrolyze a product that is as reactive as the amino ester, since it has a tendency rather to polymerize under the hydrolysis conditions.

According to yet another tested route, it was realised that cross metathesis involving an acid, such as a fatty acid or acrylic acid, for example, gives such low yields of acid nitrile (<60%) that, even followed by hydrogenation, this type of crossed metathesis does not lead simply to an amino acid.

Moreover, metathesis and/or hydrogenation catalysts have a tendency to entail the spurious formation of secondary amines in parallel with the formation of the primary amine which is the targeted amino acid.

Whereas the amino ester containing 9 carbons in the linear chain is readily purifiable by distillation, for example according to the Pechiney process described in patent FR 1 087 798, this is not the case for heavier amino esters whose main carbon chain comprises more than 9 carbon atoms. The existing processes, especially the abovementioned process, do not make it possible to solve the problem of purification for long-chain amino esters containing more than 9 carbons.

Finally, the presence in an amino acid or amino ester of impurities, even in an apparently small amount of the order of 0.5% to 1%, makes these amino acids or amino esters very difficult or even impossible to use directly as polymerization monomers, especially on account of:
N-alkylation reactions,
low degrees of polymerization (DP) obtained, which do not exceed 30, for example, In particular, the presence of impurities, such as secondary amines, induces these DP limitations, but also:
problems of pollution of the polymerized product,
coloration of the polymerized product induced by the impurities (secondary amines, but also ash: nickel, mineral salts, etc.) present in the monomers,
or problems of fouling of the polymerization device.

The aim of the present invention is thus to synthesize amino acid in high purity, in which the content of impurities, especially of secondary amines, is less than 0.5% by weight and preferably less than 0.2% by weight, by means of a simple process comprising the fewest possible steps, having a high yield of amino acid (>90%) and allowing purification and thus easy polymerization of the amino acid.

The Applicant has now found a process which, in a quite particular sequence of steps, allows this aim to be achieved.

SUMMARY OF THE INVENTION

One subject of the present invention is thus a process for synthesizing an amino acid from an unsaturated fatty compound I of formula:

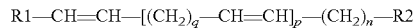

$$R1-CH=CH-[(CH_2)_q-CH=CH]_p-(CH_2)_n-R2$$

in which:
R1 is H, an alkyl radical of 1 to 11 carbon atoms comprising, where appropriate, a hydroxyl function, or (CH2)m-R4
  m is an integer in the range from 0 to 11,
  n is an integer in the range from 2 to 13,
  p is an integer, p being equal to 0, 1 or 2,
  q is an integer equal to 0 or 1,
  R2 is COOR5 or CN,
  R4 is H or R2
  R5 is an alkyl radical of 1 to 11 carbon atoms or a radical comprising two or three carbon atoms bearing one or two hydroxyl functions, or alternatively a diglyceride or a triglyceride residue in which each fatty acid of said glyceride residue is either saturated or unsaturated,
characterized in that it comprises at least the following steps:
  cross metathesis with a short unsaturated compound II,
  one of the compounds I or II comprising a nitrile function and the other of these compounds II or I an ester function, so as to obtain and recover at least one monounsaturated nitrile ester (abbreviated hereinbelow as UNE),
  hydrolysis of the UNE into an unsaturated acid nitrile (abbreviated hereinbelow as UAN).
  hydrogenation of the UAN to a saturated amino acid (abbreviated hereinbelow as AA),
  optional purification of the AA (optional step).

DESCRIPTION OF EMBODIMENTS OF THE INVENTION

For the purposes of the invention, cross metathesis (abbreviated hereinbelow as cm) is a metathesis reaction between an ester compound and a nitrile compound.
  either between an unsaturated fatty ester generally derived from oleochemistry with a short-chain unsaturated nitrile compound, such as acrylonitrile,
  or between an unsaturated fatty nitrile compound generally derived from oleochemistry with a short-chain unsaturated ester compound, such as an acrylate and, in this case, preferably methyl acrylate.

The process of the invention was developed for the purpose of exploiting starting materials derived from renewable natural sources. Use is thus preferably made, as "compound I", of an unsaturated fatty ester or an unsaturated fatty nitrile derived from a natural fatty acid. However, compound I may equally be chosen from similar unsaturated compounds obtained by chemical synthesis.

The cross metathesis is preferably performed in the presence of a metathesis catalyst of ruthenium carbene type as described later.

As starting compound I that may be used in the process of the invention, an unsaturated fatty ester or nitrile is most particularly intended, preferably of natural origin, of formula I:

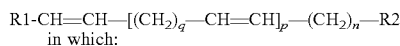
in which:

R1 is H, an alkyl radical of 1 to 11 carbon atoms comprising, where appropriate, a hydroxyl function, or $(CH_2)_m$—R4 m is an integer in the range from 0 to 11,
n is an integer in the range from 2 to 13,
p is an integer, p being equal to 0, 1 or 2,
q is an integer equal to 0 or 1,
R2 is COOR5 or CN,
R4 is H or R2
R5 is an alkyl radical of 1 to 11, preferably of 1 to 5, preferably of 1 to 4, carbon atoms or a radical comprising two or three carbon atoms bearing one or two hydroxyl functions, or alternatively a diglyceride or a triglyceride residue in which each fatty acid of said glyceride residue is either saturated or unsaturated, For the purposes of the invention, the term "fatty" compound means a compound comprising from 8 to 57 (especially in the case of a triglyceride) carbon atoms, preferably from 8 to 36 carbon atoms, preferably from 10 to 24 carbon atoms, and preferably comprising 10 or 11 carbon atoms.

Compound I comprises at least one unsaturation, i.e. a C═C double bond. Each C═C double bond of compound I may be in cis or trans conformation. The unsaturation is located in position x relative to the ester or nitrile group, this position conventionally being referred to as "delta x"). This makes it possible to determine the formula of the final ω-amino acid obtained according to the process of the invention.

The compound of formula I $R_1$—CH═CH—$[(CH_2)_q$—CH═CH$]_p$—$(CH_2)_n$—$R_2$ is advantageously chosen from fatty acid esters (including monoglycerides, diglycerides and triglycerides) or nitriles derived from fatty acids, of plant or animal origin (including those derived from natural algae).

Examples of fatty acids that may be mentioned include C10 acids, obtusilic acid (cis-4-decenoic acid) and caproleic acid (9-decenoic acid), C12 acids, lauroleic acid (cis-5-dodecenoic acid) and linderic acid (cis-4-dodecenoic acid), C14 acids, myristoleic acid (cis-9-tetradecenoic acid), physeteric acid (cis-5-tetradecenoic acid) and tsuzuic acid (cis-4-tetradecenoic acid), C16 acids, palmitoleic acid (cis-9-hexadecenoic acid), C18 acids, oleic acid (cis-9-octadecenoic acid), elaidic acid (trans-9-oxodecenoic acid), petroselinic acid (cis-6-octadecenoic acid), vaccenic acid (cis-11-octadecenoic acid) and ricinoleic acid (12-hydroxy-cis-9-octadecenoic acid), C20 acids, gadoleic acid (cis-9-eicosenoic acid), gondoic acid (cis-11-eicosenoic acid), cis-5-eicosenoic acid and lesquerolic acid (14-hydroxy-cis-11-eicosenoic acid), C22 acids, cetoleic acid (cis-11-docosenoic acid) and erucic acid (cis-13-docosenoic acid), and also the polyunsaturated acids linoleic acid and linolenic acid.

These various acids are derived from plant oils extracted from various oleagineous plants, such as sunflower, rape, castor oil plant, *Lesquerella,* olive, soya, palm tree, avocado, sea buckthorn, coriander, celery, dill, carrot, fennel, *Limnanthes alba* (meadowfoam), safflower, camelina or *Jatropha.*

They are also derived from the terrestrial or marine animal world and, in this case, either in the form of fish, mammals or algae. They are generally fats originating from ruminants, fish such as cod, or marine mammals such as whales or dolphins. However, for technical reasons of performing the metathesis reaction, it is often preferable to modify this ester or nitrile derived from a fatty acid by subjecting it to a prior reaction comprising an ethylenolysis, butenolysis or propenolysis or thermal cracking (pyrolysis) leading to a fatty ester or nitrile of formulae such as $CH_2$═CH—$(CH_2)_n$—R2, $CH_3$—CH═CH—$(CH_2)_n$—R2 or $CH_3$—$CH_2$—CH═CH—$(CH_2)_n$—R2.

Cross metathesis may equally be performed on omega-unsaturated fatty substances whose double bond is at the end of the chain, and on fatty substances whose double bond is internal, but omega-unsaturated fatty substances are preferably used. A monounsaturated and omega-unsaturated starting compound I is preferably used, and compound I is preferably a fatty ester or nitrile of formula $CH_2$═CH—$(CH_2)_n$—R2.

According to an advantageous embodiment of the process of the invention, a compound I in which R2 is COOR5 is used. Preferably, in this case, the cross metathesis on compound I is performed with a short-chain unsaturated nitrile compound II (main chain comprising less than 8 carbons).

The short-chain unsaturated nitrile compound II is advantageously chosen from: acrylonitrile, fumaronitrile, 2-butenenitrile, 1-butenenitrile, 2-pentenenitrile, 3-pentenenitrile, 4-pentenenitrile and 1-pentenenitrile, and mixtures thereof. Preferably, compound II is acrylonitrile.

An unsaturated nitrile ester (abbreviated hereinbelow as UNE) and a long-chain diester coproduct are thus formed.

Preferably, the unsaturated compound I is a monounsaturated omega-unsaturated fatty ester of formula $CH_2$═CH—$(CH_2)_n$—COOR5.

R5 is an alkyl radical comprising from 1 to 11, preferably from 1 to 5 carbon atoms, preferably from 1 to 2 carbon atoms.

According to an advantageous embodiment of the process of the invention, the omega-unsaturated fatty ester compound I, including when this omega-unsaturated fatty ester is present in the monoglyceride, diglyceride or triglyceride form, is used with an unsaturated short nitrile compound II, such as acrylonitrile, in the presence of a metathesis catalyst, preferably by continuously adding the catalyst. During this first step, in which acrylonitrile reacts, ethylene is evolved from the reaction, and a mixture of nitrile ester and diester is formed.

According to another advantageous embodiment of the process of the invention, a compound I in which R2 is CN is used.

Preferably, the unsaturated compound I is an omega-unsaturated fatty nitrile of formula $CH_2$═CH—$(CH_2)_n$—CN.

Preferably, in this case, the cross metathesis on the fatty nitrile compound I is performed with a short-chain unsaturated ester compound II (main chain comprising less than 8 carbons), preferably an acrylate, such as methyl acrylate. In this case, during this cross metathesis step, in which the acrylate reacts, ethylene is evolved from the reaction, and a mixture of nitrile ester and dinitrile is formed.

The short-chain unsaturated ester compound II is advantageously chosen from the compounds of formula: R6-HC═CH—$(CH_2)_n$—COOR7 in which:
n is 0 or 1; R6 is $CH_3$ or H; R7 is Me (methyl), Et (ethyl) or Bu (butyl). Preferably, compound II is methyl acrylate.

The metathesis reaction is performed in the presence of at least one metathesis catalyst. These catalysts are well known and an entire range of them exists. Mention may, for example, be made of the tungsten complexes developed by Schrock et al (*J. Am. Chem. Soc.* 108:2771, 1986) or Basset et al. (*Angew. Chem., Ed. Engl.* 31:628, 1992). More recently, catalysts termed Grubbs catalysts have emerged (see Grubbs et al., *Angew. Chem., Ed. Engl.* 34:2039, 1995 and *Organic Letters* 1:953, 1999) which are ruthenium-benzylidene complexes operating in homogeneous catalysis. Other studies have been carried out in order to produce immobilized catalysts, i.e. catalysts of which the active ingredient is that of the homogeneous catalyst, in particular ruthenium-carbene complexes immobilized on an inactive support.

The process according to the invention advantageously uses at least one metathesis catalyst of ruthenium-carbene type. Said ruthenium-carbene catalyst is preferably chosen from charged or uncharged catalysts of general formula:

$$(X_1)_a(X_2)_b Ru(\text{carbene } C)(L_1)_c(L_2)_d(L_3)_e$$

in which:
- a, b, c, d and e are integers, which may be identical or different, with a and b equal to 0, 1 or 2; c, d and e equal to 0, 1, 2, 3 or 4;
- $X_1$ and $X_2$, which may be identical or different, each represent a charged or uncharged and monochelating or polychelating ligand; by way of examples, mention may be made of halides, sulfate, carbonate, carboxylates, alkoxides, phenoxides, amides, tosylate, hexafluorophosphate, tetrafluoroborate, bis(trifyl)amide, an alkyl, tetraphenylborate and derivatives; $X_1$ or $X_2$ can be bonded to $L_1$ or $L_2$ or to the carbene C so as to form a bidentate or chelate ligand on the ruthenium; and
- $L_1$, $L_2$ and $L_3$, which may be identical or different, are electron-donating ligands, such as phosphine, phosphite, phosphonite, phosphinite, arsine, stilbene, an olefin or an aromatic compound, a carbonyl compound, an ether, an alcohol, an amine, a pyridine or derivative, an imine, a thioether, or a heterocyclic carbene; $L_1$, $L_2$ or $L_3$ can be bonded to the carbene C so as to form a bidentate or chelate ligand, or a tridentate ligand.

The carbene C is represented by the general formula: $CR_1R_2$ for which $R_1$ and $R_2$ are groups which may be identical or different, such as hydrogen or any other functionalized or non-functionalized hydrocarbon-based group of saturated, unsaturated, cyclic, aromatic, branched and/or linear type. By way of examples, mention may be made of ruthenium alkylidene, benzylidene, benzylidene ether or cumylene complexes, such as vinylidenes Ru=C=CHR or allenylidenes Ru=C=C=$CR_1R_2$ or indenylidenes.

A functional group (making it possible to improve the retention of the ruthenium complex in an ionic liquid) can be grafted onto at least one of the ligands $X_1$, $X_2$, $L_1$, $L_2$, or onto the carbene C. This functional group may be charged or uncharged, such as preferably an ester, an ether, a thiol, an acid, an alcohol, an amine, a nitrogenous heterocycle, a sulfonate, a carboxylate, a quaternary ammonium, a guanidinium, a quaternary phosphonium, a pyridinium, an imidazolium, a morpholinium or a sulfonium.

The metathesis catalyst can optionally be rendered heterogeneous on a support in order to facilitate the recovery/recycling thereof.

The cross metathesis catalysts of the process of the invention are preferably ruthenium carbenes described, for example, in *Aldrichimica Acta*, vol. 40, no. 2, 2007, p. 45-52.

Examples of such catalysts are Grubbs catalysts, Hoveyda-Grubbs catalysts, Piers-Grubbs catalysts, and other metathesis catalysts of the same type, whether they are "1 st-generation", "2nd-generation" or "3rd-generation" catalysts.

Grubbs catalysts are based on a ruthenium atom surrounded by 5 ligands:

2 anionic ligands, such as halides;
2 electron-donating ligands, such as trialkyl phosphines, or saturated N-heterocyclic carbenes (called NHC ligands);
an alkylidene group, such as substituted or unsubstituted methylene groups =$CR_2$.

These metathesis catalysts are classified into two categories, depending on the nature of their electron-donating ligands L:
those which contain two phosphine ligands (and no saturated NHC ligand), developed first, are 1 st-generation-type catalysts;
those which contain a saturated NHC ligand (heterocyclic carbene) are 2nd-generation-type catalysts.

A type of catalyst termed "Hoveyda-Grubbs" catalyst contains, among the electron-donating ligands, a benzylidene-ether chelating ligand, and either a phosphine (1st generation) or a saturated NHC ligand (2nd generation), usually substituted with phenyls generally substituted with mesityl (Mes) groups or else with isopropyl (iPr) groups.

Another type of catalyst termed "Piers-Grubbs" catalyst forms a four-ligand cationic complex which does not require dissociation of a ligand before the reaction.

Other types of catalysts are the "Umicore", "Zanan" and "Grela" catalysts. Generally, the choice of the catalyst depends on the reaction under consideration. According to an advantageous embodiment, the catalyst is free of phosphine.

Preferred catalysts are the catalysts which follow:
(1) The catalyst denoted "Hoveyda-Grubbs 2", having the following formula:

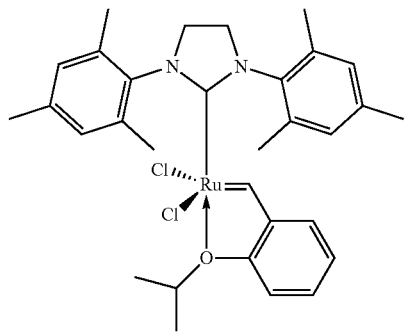

(2) The catalyst denoted "M51", having the following formula:

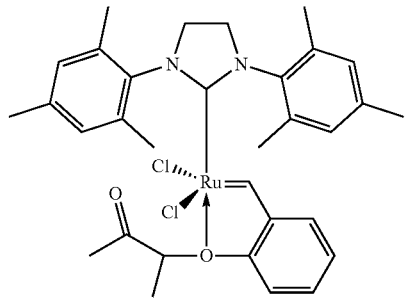

(3) The catalyst denoted "M71-SIPr", having the following formula:

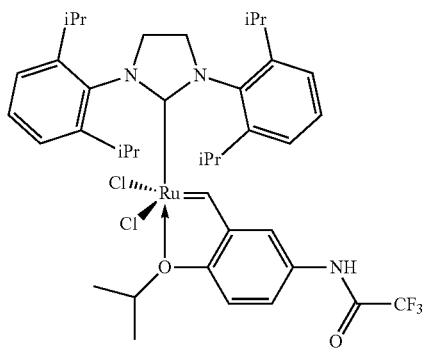

(4) The catalyst denoted "M71-SIMes", having the following formula:

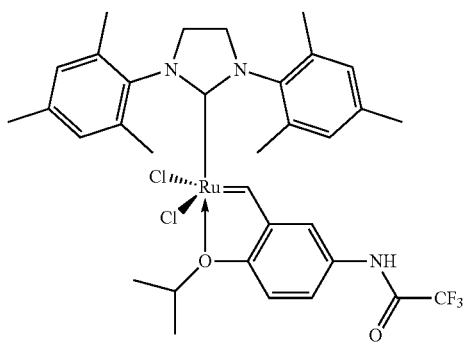

(5) The catalyst denoted "M72-SIPr", having the following formula:

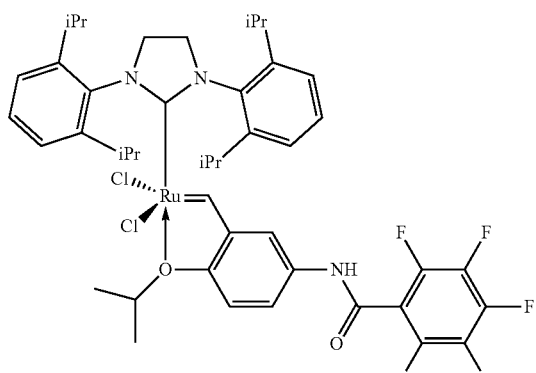

(6) The catalyst denoted "M73-SIPr", having the following formula:

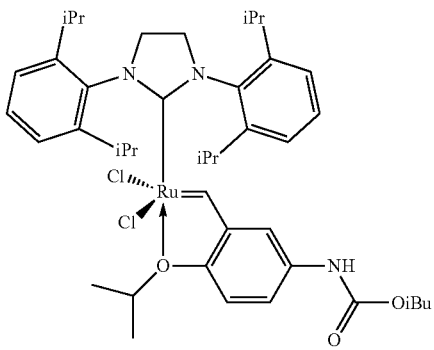

(7) The catalyst denoted "M74-SIPr", having the following formula:

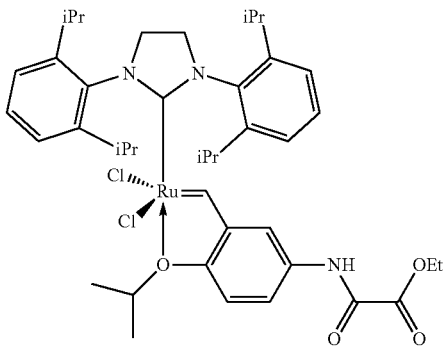

(8) The catalyst denoted "Nitro-Grela-SIMes", having the following formula:

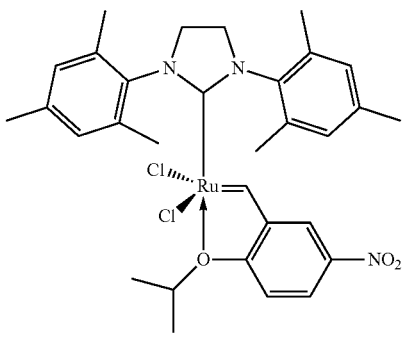

(9) The catalyst denoted "Nitro-Grela-SIPr", having the following formula:

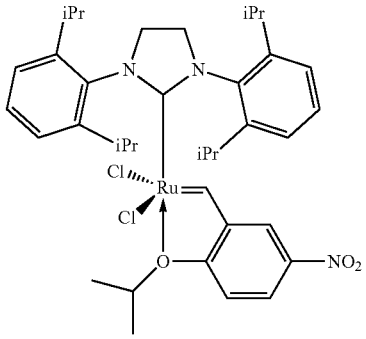

(10) The catalyst denoted "Apeiron AS2034", having the following formula:

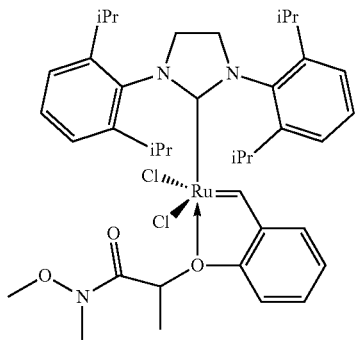

(11) The catalyst denoted "Zannan 44-0082 (Strem)", having the following formula:

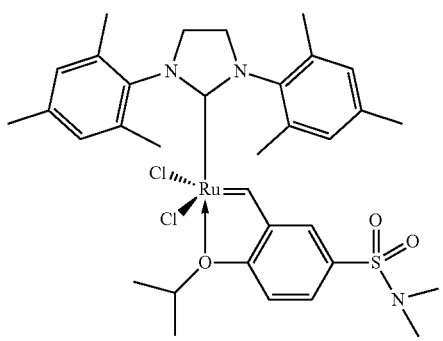

(12) The catalyst denoted "M831-SIPr", having the following formula:

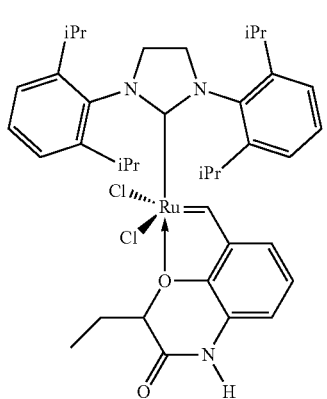

(13) The catalyst denoted "M832-SIPr", having the following formula:

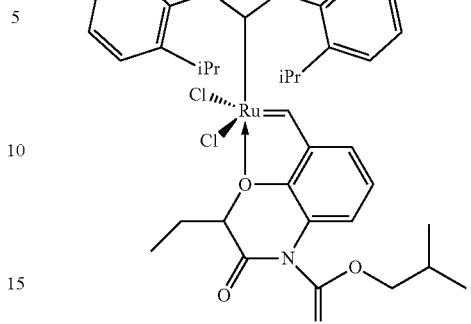

(14) The catalyst denoted "M853-SIPr", having the following formula:

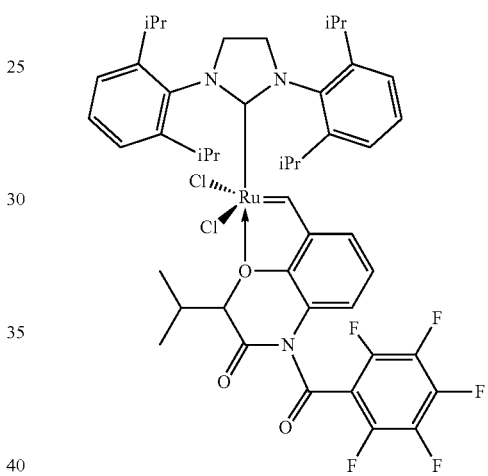

(15) The catalyst denoted "M863-SIPr", having the following formula:

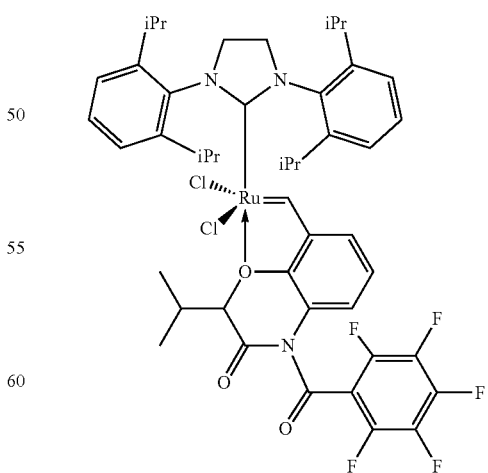

(16) The catalyst denoted "Materia C711", having the following formula:

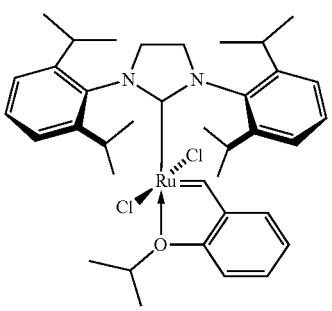

The metathesis reaction is preferably performed in liquid medium under the following operating conditions.

The temperature is generally in the range from 20 to 160° C. and preferably in the range from 20 to 120° C.

The pressure is generally in the range from 1 to 30 bar. The reaction is preferably performed at low pressure in the range from 1 to 10 bar and more preferably at atmospheric pressure when the boiling point of the reagents used makes it possible. Specifically, if a mild evolution of olefin, ethylene or the like, is always intended, it is advantageous to work at low pressure, preferably atmospheric pressure.

The reaction may be performed without solvent or in the presence of at least one solvent, such as toluene, xylenes, dichloromethane, dimethyl carbonate or diethyl carbonate, for example, and mixtures thereof.

After the cross metathesis, a UNE (the product) and, depending on the case, a DE or a DN (the coproduct) are obtained. Although the subsequent steps of the process can be performed directly on this mixture of products derived from cross metathesis, it is preferable to isolate the UNE in order to optimize the hydrolysis and hydrogenation yields of the process of the invention. Optionally, the product is thus readily separated and recovered from the cross metathesis coproduct by distillation and/or any other means well known to those skilled in the art. Use may especially be made of liquid/liquid extraction (for example to separate out any solvent), crystallization (for example to separate out the coproduct) or adsorption (for example to separate out the catalyst).

The process of the invention also comprises, after the cross metathesis step described above, hydrolysis of the unsaturated nitrile ester UNE into an unsaturated acid nitrile (referred to hereinbelow as UAN).

The hydrolysis may be performed according to various well-known processes for hydrolyzing the ester function without hydrolyzing the nitrile function of the UNE. The hydrolysis may especially be performed as described in the documents *CEH—Natural Fatty Acids*, by Michael P. Malveda, page 11, at atmospheric pressure, for example in the presence of sulfuric acid and sulfonic acid or under pressure, in batch or discontinuous mode, in the presence of a catalyst such as zinc oxide or magnesium oxide and water. An acidic or basic catalyst may be used. The hydrolysis may also be performed according to the process similar to that described on page 314, III.1.3 of *Procédés de prétrochimie*, volume 2, by A. Chauvell, G. Lefebvre and L. Castex.

Among the hydrolysis processes that may be used in the process of the invention, mention may be made especially of the following four processes:

low-temperature hydrolysis (15° C.-60° C.) in the presence of sodium hydroxide (saponification);

medium-temperature hydrolysis (60° C.-120° C., preferably from 60 to 100° C. or better still at about 80° C.) in solvent medium and under acidic catalysis;

high-temperature hydrolysis (120° C.-300° C., preferably 130° C.-250° C.) under pressure;

enzymatic hydrolysis, generally at low temperature, but more broadly at a temperature in the range from 10° C.-100° C., preferably from 10° C. to 40° C.

Although the subsequent hydrogenation step of the process can be performed directly on the product derived directly from the hydrolysis, it is preferable to isolate the UAN in order to optimize the hydrogenation yield of the process of the invention, especially by crystallization, distillation and/or any other means well known to those skilled in the art.

The process according to the invention also comprises, after the hydrolysis step, hydrogenation of the UAN into AA.

The hydrogenation is performed in the presence of at least one hydrogenation catalyst, according to various well-known processes. Examples of suitable catalysts are those containing elements from group VIII of Mendeleev's Periodic Table of the Elements, namely iron, cobalt, nickel and noble metals, such as ruthenium, rhodium, palladium, osmium, iridium and platinum, alone or as a mixture. These metals may optionally be doped with gold. The group VIII elements may be present in the catalyst in the form of the metal or of its oxide. The element may be used in the form of a catalyst of the Raney type. The group VIII element present in metal form or in the form of a compound may be used as a mixture with larger or smaller amounts of one or more compounds of other elements. The catalyst may be in finely divided form, or in the form of granules, or alternatively may be deposited on a support.

Examples of suitable supports are: silica, pumice, titanium dioxide, carbon, charcoal, silicon carbide or alumina. Examples of preferred catalysts are the following: nickel catalysts, Raney nickel, cobalt catalysts, for example Raney cobalt, and cobalt oxides, as a mixture with other compounds such as phosphates, and also platinum catalysts. The platinum catalysts may be catalysts containing platinum bound to charcoal, Pt/C, manufactured via well-known techniques and containing platinum in metal form. Use may also be made of Adams' catalyst, which is introduced into the reactor in $PtO_2$ form and which is reduced in situ to finely divided platinum metal.

The reaction may be performed in the liquid phase by mixing the material to be hydrogenated with a solvent. When hydrogenation catalysts formed from precious metals, for example Pt/C, are used, it may be judicious for the solvent to contain acetic acid alone or with another liquid, for example water.

When Raney nickel or Raney cobalt is used, or alternatively catalysts formed from oxides of the group VIII metals bound to supports, examples of suitable solvents that may be mentioned include alcohols, especially lower alcohols, for example those containing from 1 to 8 carbon atoms per molecule. Examples of lower alcohols are ethanol and propanols, such as n-propanol and isopropanol.

The alcohol is preferably used as a mixture with water and it is particularly judicious to add ammonia.

It is not observed that the proportion of by-products such as secondary amines is reduced by the addition of ammonia.

The molar ratio of ammonia to the total amount of UAN initially present may be, for example, from about 1 to 1000, preferably from 60 to 600, in particular from 150 to 300.

The solution is placed in contact with the catalyst in any suitable manner and hydrogen is brought into contact with the catalyst and the solution.

In the case where a finely divided catalyst is used, it may be dispersed in the solution, and maintained in dispersion by stirring the solution.

An easy means for performing the hydrogenation consists in using a bed of pellets or granules of solid catalyst. A solution of the material to be hydrogenated may be passed over the catalyst, by flow in the same direction or in counter-current to a hydrogen stream. The bed may be completely immersed in the solution, or the bed may be used in the form of a trickle bed. In this case, the bed is surrounded with gaseous hydrogen and the solution of the material to be hydrogenated can infiltrate through the bed.

The reaction may be performed in batch form via successive loads or continuously.

The optimum temperature and pressure for the hydrogenation depend on the catalyst used. When catalysts based on noble metals are used, for example Pt/C, the hydrogenation may be performed under a range of conditions such as: from 15° C. to 100° C. and under a pressure from 1 atm to 100 atm. However, greater selectivity is obtained at temperatures of 50 to 60° C. and pressures of 60 to 80 atm. When nickel and cobalt hydrogenation catalysts are used, temperatures from 10 to 200° C. and pressures of 1 and 350 atm may advantageously be used. The reaction duration obviously depends on the reaction conditions, and the reaction time may range from less than 20 minutes to more than 5 hours.

The saturated amino acid (abbreviated as AA in the present description) produced during the hydrogenation reaction may be recovered in any appropriate manner. To facilitate the recovery, it is judicious, in particular when the process is performed under pressure, to equip the hydrogenation reactor with an inner filter placed below the level of the liquid and arranged so as to prevent any obstruction (for example by the catalyst) of the outlet serving for recovering the product, and such that the filter can be readily cleaned by passing hydrogen through the filter.

The product is advantageously withdrawn through this filter, so that it is collected without catalyst. When a hot reaction mixture is used, the product is preferably withdrawn at the reaction temperature to prevent the separation of the product in the reactor or in the pipes leaving the reactor. The product may be taken out intermittently or continuously, but, in both cases, it is desirable to maintain an atmosphere of hydrogen on the catalyst so as to avoid its deactivation. The saturated amino acid AA may be recovered by cooling the solution withdrawn from the reactor and/or evaporating the solvent.

According to an advantageous embodiment of the process of the invention, the hydrogenation is performed in the presence of at least one metal catalyst chosen from ruthenium, rhodium, palladium and platinum supported on a silicon carbide support. The hydrogenation temperature is in the range from 10 to 300° C. and preferably from 20-200° C., and the pressure is in the range from 1 bar 300 bar. A mixture of a lower alcohol and water, and of ammonia present in the reaction system, is advantageously used as solvent. These hydrogenation conditions make it possible to reduce or even eliminate the parallel production of secondary amines.

Use is thus preferably made of a hydrogenation catalyst in which ruthenium, rhodium, palladium or platinum or a mixture of two or more of these metals (optionally doped with gold) are loaded onto a silicon carbide support. The amount of the various abovementioned metals loaded onto the silicon carbide support is advantageously from 0.1% to 10% by weight and preferably from 0.2% to 1% by weight. The purity of the silicon carbide support is in the range from 70% to 100%. The support may comprise up to 30% of impurities such as: silica, alumina, carbon, iron oxide, calcium oxide, sodium oxide, potassium oxide, etc. The purity of the silicon carbide support in the process of the invention is preferably very high, and preferably characterized by: the absence of iron and the absence (of a layer) of surface silica, which are the two major impurities of SiC. For the silicon carbide support, use is preferably made of a material with a porosity in the range from 20% to 60% and whose pore size is in the range from 1 to 200 µm, and it is preferable to clean it with mineral acid and a basic aqueous solution, before the production of the catalyst, especially to remove the Fe and SiO2 impurities.

The catalysts may be prepared via the methods known for charging metals onto a support. For example, a catalyst may be prepared by dissolving ruthenium trichloride, rhodium trichloride, palladium dichloride, chloroplatinic acid or a mixture of two or more thereof in water to form an aqueous solution, and leaving it in contact with the silicon carbide support to charge the various metal compounds mentioned above onto the support, followed by activating the catalyst via heating means and reduction in a stream of hydrogen. Furthermore, in this preparation process comprising the impregnation of various metal compounds mentioned above into the support, the heating and reduction in a stream of hydrogen are preferably repeated several times. Other preparation processes comprise:

- processes in which nitrates or acetates of various metals are dissolved in water or an organic solvent such as benzene, chloroform or alcohol, or alternatively in a mixture of water and organic solvent, and impregnated into the support, and the various metal components that have been impregnated into the support are then heat-treated or treated with an alkali and transformed into oxides or hydroxides, and/or
- processes in which the heating and reduction are performed in a stream of a reducing gas comprising formaldehyde, formic acid or methanol, in which a base is added to a solution of formic acid or formaldehyde.

The conditions of the hydrogenation reaction for forming the amino acid are preferably a temperature in the range from 10 to 200° C. and preferably from 70 to 130° C., and a pressure ranging from 1 bar to 350 bar and preferably from 5 to 150 bar.

The use of a solvent is preferred during the hydrogenation of the long-chain UAN (comprising more than 9 C) of the invention. Mixtures of lower alcohols and water may be used as solvent. The lower alcohol is preferably chosen from n-propanol, isopropanol, n-butanol and isobutanol. The respective proportions of the mixture of lower alcohol and water are advantageously in the range from 5:1 to 1:5 by volume.

The source of hydrogen used may be pure hydrogen or hydrogen diluted with an inert gas, for instance nitrogen, and the amount of hydrogen used is preferably in the range from 2 to 200 mol per 1 mol of UAN. This has the advantage, when ammonia is present in the reaction system, of eliminating the production of secondary amine. The amount of ammonia used is preferably in the range from 1 to 100 mol per 1 mol of UAN.

The hydrogenation reaction may be performed in batch or continuous mode, but is preferably performed continuously. In continuous mode, use is advantageously made of a reactor in which the catalyst is provided via streams that are opposite or parallel to the streams of UAN materials and of hydrogen, and preferably the catalyst is in a fixed bed.

The hydrogenation catalyst prepared as described above conserves a high level of activity in a continuous reaction over a long period of time and the AA is obtained in a high yield of 98% or more. Furthermore, since the mechanical strength of the catalyst is high, there is virtually no disintegration or degradation (as opposed to the majority of catalysts on charcoal) of the catalyst even after the reaction has been performed continuously for long periods of time, of several hours.

According to an advantageous embodiment, the hydrogenation is performed in the presence of a noble metal catalyst and of a chemical substance having a polydentate ligand which forms a chelate by bonding with metal ions is added to the reaction system. The aforementioned chemical substance added with the noble metal catalyst forms a chelate that is soluble in water with heavy metals mainly such as iron and nickel, and it may be chosen from: polyaminocarboxylic acids, such as ethylenediaminetetraacetic acid (EDTA), hydroxycarboxylic acids such as citric acid, and condensed phosphates, etc. The amount of this chemical substance added is in the range from 0.001 to 0.1 part by weight per 100 parts by weight of the liquid filler fed into the hydrogenation reactor (including the catalyst), and preferably from 0.002 to 0.01 part by weight. In addition, the aforementioned chemical substance may be added in the form of an aqueous solution or in the form of a solid added to the feed as a liquid. This particular hydrogenation embodiment allows the catalyst to conserve high activity during the reaction when it is continued over a long period, the amount of heavy metals and of ash contained in the hydrogenation reaction product is thus considerably reduced, and there is no appreciable coloration of the reaction product.

The saturated amino acid AA thus obtained according to the process of the invention may be purified, if so desired, preferably by recrystallization from a suitable solvent.

In this case, the process of the invention also comprises, after the hydrogenation step, a step of purifying the AA, so as to remove the impurities, especially the secondary amine impurities below a threshold <0.5% by weight, preferably <0.2% by weight, relative to the weight of AA.

Any suitable purification means may be used in this step. Mention may be made especially of the process of purification by crystallization. The AAs obtained according to the process, the carbon number of which is greater than 9, are in particular readily recrystallizable from any suitable solvent. Such a process is described, for example, in patent FR 1 574 471 from the company BP Chemicals.

Advantageously, the process of the invention uses a purification according to a process in which the product of hydrogenation of the UAN is recrystallized from an aqueous solution containing a lower aliphatic alcohol and ammonia. This process is especially described in patent JP48-6445 B.

Advantageously, the purification of the AA is performed by crystallization and preferably comprises at least two successive crystallization steps:

(A) a step in which crude AA crystals are isolated, after dissolution of the hydrogenation product (AA obtained) in an aqueous solution containing a lower aliphatic alcohol and an aqueous solution containing ammonia, in a first crystallization device maintained at a temperature in the range from 0-30° C., and (B) a step in which pure AA crystals are isolated, after redissolution of the crude AA crystals obtained in step A in an aqueous solution containing a lower aliphatic alcohol and ammonia in a second crystallization device maintained at a temperature in the range from 30-60° C.

Each of the steps of the process of the present invention is explained in specific terms below.

Step (A):

The hydrogenation product (AA) may contain as by-products: especially secondary amines and unreacted UAN reagents. Consequently, for the purpose of removing these impurities, the AA is dissolved in an aqueous solution containing a lower aliphatic alcohol and ammonia, and is then introduced into a first crystallization tank at a temperature in the range from 0-30° C., and the crude AA crystals mainly containing the AA, and the mother liquor containing the secondary amines and UAN, are then separated. As lower aliphatic alcohol used in the aqueous solution, use is made of a C1-4 linear-chain or branched-chain alcohol, such as n-propanol, isopropanol, n-butanol or isobutanol, for example. The volume ratio of the lower aliphatic alcohol relative to the water is preferably between 1:10-10:1 and preferably in the range from 1:3-3:1. The ratio of ammonia relative to the mixture of lower alcohol and water may vary within a wide range, for example from 1% by weight to saturation. In addition, the concentration of the product containing the AA relative to the aqueous solution containing the lower aliphatic alcohol and ammonia is preferably in the range from 1-10% by weight and particularly preferably in the range from 2-8% by weight.

While maintaining the temperature of the first crystallization tank at 0-30° C. (which is a lower temperature than the second crystallization tank below), the solution is separated into crude crystals mainly containing the AA and a mother liquor which contains secondary amines and UAN.

The crude AA crystals are transferred into the following step (B).

Moreover, fresh UAN is added to the mother liquor, which is then dissolved and hydrogenated, and then recycled into the abovementioned first crystallization device (tank).

Step (B):

The abovementioned crude AA crystals isolated in step A may still contain impurities, in very small amounts. The crude AA crystals are thus dissolved in an aqueous solution containing a lower aliphatic alcohol and ammonia, and then introduced into a second crystallization reservoir and then separated at a temperature of 30-60° C. into pure AA crystals, on the one hand, and a mother liquor which contains the secondary amines and the UAN, on the other hand.

As aqueous solution containing a lower aliphatic alcohol and ammonia, an aqueous solution similar to that used in step A may be used. Use may also be made of the same ratio of AA relative to the aqueous solution as in step (A). As aqueous solution containing a lower aliphatic alcohol and ammonia, use may be made of a freshly prepared solution or mother liquor isolated in the second crystallization tank may be recycled and reused.

The second crystallization tank is maintained at a higher temperature than the first crystallization tank, i.e. a temperature of 30-60° C., so that the rest of the impurities present in the crude crystals derived from the first crystallization are transferred into the mother liquor. Consequently, the pure AA crystals obtained after the separation in the second crystallization reservoir are of high purity, and the use of crystallization at high temperature makes it possible to increase the growth and size of the crystals, which facilitates the separation. The mother liquor obtained after step B may be redistributed, respectively, into the first crystallization device and/or the second crystallization device as solvent for the AA.

The sequence of steps in the process of the invention described above makes it possible to facilitate the AA purification step, and in particular facilitates:

the removal of the initial metathesis reagent by distillation,
the removal of the coproduct,
the removal of the metathesis catalyst,
the removal of the secondary amine,
the hydrolysis and thus removal of the source of methanol leading to the N-methylation reactions, and
the final product obtained is not colored.

Furthermore, the amino acid produced by the process of the invention is directly usable in existing polymerization units, whereas, to use an amino ester, dedicated lines associated with the flammability of methanol, for example, are necessary.

The purification according to the process of the present invention makes it possible to crystallize and to isolate even purer AA from the hydrogenation product.

Specifically, the content of impurities, such as heavy metals, in the final product obtained by standard purification by crystallization is considerably reduced (going from 0.3-0.5 ppm to 0.1 ppm or less) and the content of ash (mineral residues) is considerably reduced (going from 3-6 ppm to 1-1.5 ppm).

Advantageously, the process of the present invention also comprises a step of polymer synthesis, especially of polyamide, by polymerization using the amino acid obtained after the hydrogenation step or after the purification step. Degrees of polymerization much higher than 30 are obtained according to this process. The amino acid produced according to the process of the invention, and similarly the polymer manufactured from this monomer, also have the advantage of being colorless products.

A subject of the present invention is also a polymer obtained by polymerization using the amino acid synthesized according to the process described above.

The polymers thus obtained according to the process of the invention have a high melt viscosity, and there is no notable coloration.

EXAMPLES

Example 1

Not in Accordance with the Invention

Metathesis-Hydrogenation Route 15 g of methyl 9-decenoate (81 mmol) prepared according to Example 1 of patent US 2011/0 113 679 and purified on alumina, 2.15 g of acrylonitrile (40.5 mmol) and 150 g of toluene predried over molecular sieve are introduced in a 250 ml glass reactor purged with nitrogen. The mixture is heated to 110° C. and 2.58 g of acrylonitrile (48.6 mmol) and 2 mg of M71-SiPr catalyst ($2.4 \times 10^{-3}$ mmol, supplied by the company Umicore) dissolved in 5 ml of toluene are introduced via syringes mounted on syringe drivers, over a period of 2 hours.

The reaction mixture is analyzed by GC. The conversion of the methyl 9-decenoate is 85%. The selectivity toward C11 unsaturated nitrile ester is 80%.

The metathesis reaction mixture is transferred into a 300 ml autoclave. 1.5 g of Raney nickel washed with methanol are placed in the autoclave. The autoclave is purged with nitrogen, 1 g of ammonia (59 mmol) are then introduced and the system is pressurized to 40 bar of hydrogen. The mixture is heated to 90° C. and left to react for 4 hours.

The reaction mixture is analyzed by GC. The conversion of the C11 unsaturated nitrile ester is 100%.

The reaction mixture is filtered, the toluene is evaporated off under vacuum and the residue is then distilled. 7.1 g of C11 amino ester are thus obtained (boiling point=126-130° C. at 3 mbar). The distillation yield is 60%.

This example shows that the yield is penalized by a start of polymerization of the amino ester during the distillation.

Example 2

Not in Accordance with the Invention

Metathesis-Hydrogenation-Hydrolysis Route

The metathesis reaction mixture obtained from Example 1 is evaporated under vacuum to remove the toluene and then distilled under vacuum to recover the C11 nitrile ester (boiling point=122° C. at 0.8 mbar).

10 g of C11 unsaturated nitrile ester (47.8 mmol), 100 g of toluene and 1 g of Raney nickel washed with methanol are placed in a 300 ml autoclave. The autoclave is purged with nitrogen, 1 g of ammonia (59 mmol) are then introduced and the system is pressurized to 40 bar of hydrogen. The mixture is heated to 90° C. and left to react for 4 hours.

The reaction mixture is analyzed by GC. The conversion of the C11 unsaturated nitrile ester is 100%.

The hydrogenation reaction mixture is filtered, evaporated under vacuum to remove the toluene and then transferred into a reactor containing 100 g of water. The mixture is refluxed for 24 hours. The reaction mixture is then concentrated under vacuum, filtered at 50° C. over active charcoal, and then cooled. 2.9 g of 11-aminoundecanoic acid are obtained in the form of white crystals (yield=30%).

This example shows that the hydrolysis reaction on the amino ester is inefficient.

Example 3

Not in Accordance with the Invention

Hydrolysis-Metathesis-Hydrogenation Route

Methyl 9-decenoate is converted into 9-decenoic acid. 30 g of methyl 9-decenoate (0.16 mol) and 160 ml of 1M sodium hydroxide (0.16 mol) are placed in a 500 ml reactor. The mixture is heated at 50° C. for 1 hour. It is allowed to cool to room temperature, and 160 ml of 1M hydrochloric acid (0.16 mol) are then added. The resulting mixture is extracted twice with 300 ml of dichloromethane. The dichloromethane is evaporated off and 26.3 g of 9-decenoic acid are recovered.

15 g of 9-decenoic acid (88 mmol) purified on alumina, 2.33 g of acrylonitrile (44 mmol) and 150 g of toluene predried over molecular sieve are introduced in a 250 ml glass reactor purged with nitrogen. The mixture is heated to 110° C. and 2.8 g of acrylonitrile (52.8 mmol) and 2.2 mg of M71-SiPr catalyst ($2.4 \times 10^{-3}$ mmol) dissolved in 5 ml of toluene are introduced via syringes mounted on syringe drivers, over a period of 2 hours.

The reaction mixture is analyzed by GC. The conversion of the 9-decenoic acid is 30%.

This test shows that the metathesis reaction is much less efficient on 9-decenoic acid than on methyl 9-decenoate.

Example 4

Methyl 9-Decenoate-Acrylonitrile Metathesis 15 g of methyl 9-decenoate (81 mmol) purified on alumina, 2.15 g of acrylonitrile (40.5 mmol) and 150 g of toluene predried over molecular sieve are introduced in a 250 ml glass reactor purged with nitrogen. The mixture is heated to 110° C. and 2.58 g of acrylonitrile (48.6 mmol) and 2 mg of M71-SiPr catalyst ($2.4 \times 10^{-3}$ mmol, supplied by the company Umicore) dissolved in 5 ml of toluene are introduced via syringes mounted on syringe drivers, over a period of 2 hours.

The reaction mixture is analyzed by GC. The conversion of the methyl 9-decenoate is 85%. The selectivity toward C11 unsaturated nitrile ester is 80%.

The toluene is evaporated off under vacuum and the residue is then distilled under vacuum. 11.2 g of C11 unsaturated nitrile ester are obtained (53.5 mmol, boiling point=122° C. at 0.8 mbar).

Example 5

Hydrolysis of the Nitrile Ester 10 g of C11 unsaturated nitrile ester (47.8 mmol) and 100 g of a 50/50 acetic acid/water mixture are introduced in a 250 ml glass reactor purged with nitrogen. The mixture is refluxed for 4 hours.

The reaction mixture is analyzed by GC. The conversion of the nitrile ester is 95%. The selectivity toward C11 unsaturated acid nitrile is 100%. The product is recovered by evaporation of the acetic acid, the methanol and the water.

Example 6

Hydrogenation of the Acid Nitrile

The ruthenium-on-silicon carbide catalyst used for the hydrogenation step is prepared according to Example 1 of patent JP 51-127 022.

5 g of C11 unsaturated acid nitrile (25.6 mmol), 100 g of a 50/50 solution of n-propanol and 20% aqueous ammonia and 3 g of Ru/SiC catalyst are introduced in a 300 ml autoclave. The autoclave is closed, purged with nitrogen and then pressurized to 40 bar of hydrogen. The mixture is heated to 110° C. and left to react for 2 hours. The system is depressurized and the catalyst is filtered off at 70° C. The solvent is evaporated off under vacuum and the 11-aminoundecanoic acid precipitates in the form of white crystals. The conversion is greater than 95% and the selectivity is greater than 95%. The content of secondary amine is less than 0.5%.

The invention claimed is:

1. A process for synthesizing an amino acid from an unsaturated fatty compound I of formula:

$$R_1-CH=CH-[(CH_2)_q-CH=CH]_p-(CH_2)_n-R_2$$

in which:

$R_1$ is H, an alkyl radical of 1 to 11 carbon atoms, optionally comprising a hydroxyl function, or $(CH_2)_m-R_4$ m is an integer in the range from 0 to 11, n is an integer in the range from 2 to 13, p is an integer, p being equal to 0, 1 or 2, q is an integer equal to 0 or 1, $R_2$ is $COOR_5$ or CN, $R_4$ is H or $R_2$ $R_5$ is an alkyl radical of 1 to 11 carbon atoms or a radical comprising two or three carbon atoms bearing one or two hydroxyl functions, or alternatively a diglyceride or a triglyceride residue in which each fatty acid of said glyceride residue is either saturated or unsaturated, wherein the process comprises at least the following steps:

cross metathesis with a unsaturated compound II, the unsaturated compound II having a main chain comprising less than 8 carbons, one of the compounds I or II comprising a nitrile function and the other of these compounds II or I an ester function, so as to obtain and recover at least one monounsaturated nitrile ester UNE;

hydrolysis of the UNE into an unsaturated acid nitrile UAN;

hydrogenation of the UAN into a saturated AA; and optional purification of the AA.

2. The process as claimed in claim 1, in which compound I is chosen from fatty acid esters or nitriles derived from fatty acids, chosen from: obtusilic acid (cis-4-decenoic acid) and caproleic acid (9-decenoic acid), lauroleic acid (cis-5-dodecenoic acid) and linderic acid (cis-4-dodecenoic acid), myristoleic acid (cis-9-tetradecenoic acid), physeteric acid (cis-5-tetradecenoic acid) and tsuzuic acid (cis-4-tetradecenoic acid), palmitoleic acid (cis-9-hexadecenoic acid), oleic acid (cis-9-octadecenoic acid), elaidic acid (trans-9-oxodecenoic acid), petroselinic acid (cis-6-octadecenoic acid), vaccenic acid (cis-11-octadecenoic acid) and ricinoleic acid (12-hydroxy-cis-9-octadecenoic acid), gadoleic acid (cis-9-eicosenoic acid), gondoic acid (cis-11-eicosenoic acid), cis-5-eicosenoic acid and lesquerolic acid (14-hydroxy-cis-11-eicosenoic acid), cetoleic acid (cis-11-docosenoic acid) and erucic acid (cis-13-docosenoic acid), and also the polyunsaturated acids linoleic acid and linolenic acid.

3. The process as claimed in claim 1, in which compound I is chosen from:

$CH_2=CH-(CH_2)_n-R_2$,
$CH_3-CH=CH-(CH_2)_n-R_2$, or
$CH_3-CH_2-CH=CH-(CH_2)_n-R_2$.

4. The process as claimed in claim 1, in which $R_2$ is $COOR_5$, the unsaturated nitrile compound II being chosen from: acrylonitrile, fumaronitrile, 2-butenenitrile, 1-butenenitrile, 2-pentenenitrile, 3-pentenenitrile, 4-pentenenitrile and 1-pentenenitrile, and mixtures thereof.

5. The process as claimed in claim 1, in which $R_2$ is CN, the unsaturated ester compound II being chosen from the compounds of formula:

$$R_6-HC=CH-(CH_2)n-COOR_7$$

in which n is 0 or 1; $R_6$ is $CH_3$ or H; $R_7$ is Me, Et or Bu.

6. The process as claimed in claim 1, in which the cross metathesis step uses at least one ruthenium-carbene catalyst chosen from the charged or uncharged catalysts of general formula:

$$(X_1)_a(X_2)_b Ru(\text{carbene C})(L_1)_c(L_2)_d(L_3)_e$$

in which:

a, b, c, d and e are integers, which may be identical or different, with a and b equal to 0, 1 or 2; c, d and e equal to 0, 1, 2, 3 or 4;

$X_1$ and $X_2$, which may be identical or different, each represent a charged or uncharged and monochelating or polychelating ligand; by way of example, mention may be made of halides, sulfate, carbonate, carboxylates, alkoxides, phenoxides, amides, tosylate, hexafluorophosphate, tetrafluoroborate, bis(triflyl)amide, an alkyl, tetraphenylborate and derivatives; $X_1$ or $X_2$ can be bonded to $L_1$ or $L_2$ or to the carbene C so as to form a bidentate or chelate ligand on the ruthenium; and $L_1$, $L_2$ and $L_3$, which may be identical or different, are electron-donating ligands, such as phosphine, phosphite, phosphonite, phosphinite, arsine, stilbene, an olefin or an aromatic compound, a carbonyl compound, an ether, an alcohol, an amine, a pyridine or derivative, an imine, a thioether, or a heterocyclic carbene; $L_1$, $L_2$ or $L_3$ can be bonded to the carbene C so as to form a bidentate or chelate ligand, or a tridentate ligand.

7. The process as claimed in claim 1, wherein the process includes the use of a catalyst of formula:

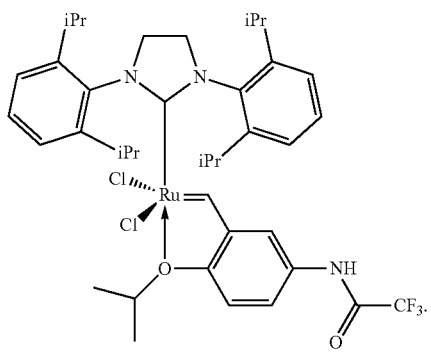

8. The process as claimed in claim 1, wherein the metathesis step is performed in liquid medium at a temperature in the range from 20 to 160° C. and at a pressure in the range from 1 to 30 bar.

9. The process as claimed in claim 1, wherein the metathesis is performed in the presence of a solvent.

10. The process as claimed in claim 1, in which the hydrolysis step comprises at least one of the following processes:
    low-temperature hydrolysis in the presence of sodium hydroxide, by saponification;
    medium-temperature hydrolysis in solvent medium and under acidic catalysis;
    high-temperature hydrolysis under pressure;
    enzymatic hydrolysis,
    and mixtures thereof.

11. The process as claimed in claim 1, in which the hydrogenation step is performed in the presence of at least one metal catalyst chosen from ruthenium, rhodium, palladium and platinum supported on a silicon carbide support.

12. The process as claimed in claim 1, in which the hydrogenation temperature is in the range from 10 to 300° C. and the pressure is in the range from 1 bar to 300 bar.

13. The process as claimed in claim 1, in which the hydrogenation step is performed in the presence of a solvent comprising a mixture of a lower alcohol and water.

14. The process as claimed in claim 1, in which the hydrogenation is performed in the presence of a noble metal catalyst and of a chemical substance bearing a polydentate ligand.

15. The process as claimed in claim 1, in which the purification comprises at least one step of recrystallization of the product derived from the hydrogenation in an aqueous solution containing a lower aliphatic alcohol and ammonia.

16. The process as claimed in claim 1, in which the purification comprises at least two successive crystallization steps:
    (A) a step in which crude AA crystals are isolated, after dissolution of the hydrogenation product in an aqueous solution containing a lower aliphatic alcohol and an aqueous solution containing ammonia, in a first crystallization device maintained at a temperature in the range from 0 to 30° C., and
    (B) a step in which pure AA crystals are isolated, after redissolution of the crude AA crystals obtained in step A in an aqueous solution containing a lower aliphatic alcohol and ammonia in a second crystallization device maintained at a temperature in the range from 30 to 60° C.

17. The process as claimed in claim 1, also comprising a step of polyamide synthesis by polymerization using the amino acid.

* * * * *